United States Patent
Burns et al.

(10) Patent No.: US 6,939,966 B2
(45) Date of Patent: Sep. 6, 2005

(54) RADIOLABELED NEUROPEPTIDE Y Y5 RECEPTOR ANTAGONISTS

(75) Inventors: H. Donald Burns, Harleysville, PA (US); Raymond E. Gibson, Holland, PA (US); Terence G. Hamill, Lansdale, PA (US); Takehiro Fukami, Hanamuro (JP)

(73) Assignees: Merck & Co., Inc., Rahway, NJ (US); Banyu Pharmaceutical Co., Ltd. (JP)

( * ) Notice: Subject to any disclaimer, the term of this patent is extended or adjusted under 35 U.S.C. 154(b) by 0 days.

(21) Appl. No.: 10/484,551

(22) PCT Filed: Jul. 19, 2002

(86) PCT No.: PCT/US02/23044
§ 371 (c)(1),
(2), (4) Date: Jan. 22, 2004

(87) PCT Pub. No.: WO03/010175
PCT Pub. Date: Feb. 6, 2003

(65) Prior Publication Data
US 2004/0192705 A1 Sep. 30, 2004

Related U.S. Application Data

(60) Provisional application No. 60/307,499, filed on Jul. 24, 2001.

(51) Int. Cl.$^7$ .................. C07D 491/10; A61K 49/00; A61K 51/00
(52) U.S. Cl. .................. 544/331; 546/16; 424/1.81; 424/1.85; 424/1.89; 424/9.2
(58) Field of Search .................. 544/331; 546/16; 424/1.81, 1.85, 1.89, 9.2; 514/278

(56) References Cited

U.S. PATENT DOCUMENTS 6,326,375 B1 12/2001 Fukami et al.

FOREIGN PATENT DOCUMENTS

WO  WO 01/14376  3/2001

OTHER PUBLICATIONS

Kalra et al., Phys. & Behavior 50 (1991), p. 5–9, "Structure–function analysis of stimulation of food intake by neuropeptide Y: Effects of receptor agonists".

Gribble et al., Tetrahedron Lett., vol. 21 (1980), pp. 4137–4140, "Regioselective ortho lithiation of halopyridines".

Mallet et al., Tetrahedron, vol. 38 (1982), pp. 3035–3042, "Reaction de la bromo–3 pyridine avec le diisopropylamidure de lithium . . . ".

Corey et al., Tetrahedron Lett., vol. 24 (1983), pp. 3291–3294, "Synthesis of a new series of potent inhibitors of thromboxane A2 biosynthesis".

Jones et al., Tetra. Letters, vol. 37 (1996), pp. 8049–8052, "Pyridine radicals in synthesis: a formal total synthesis of (±)–oxerine".

Gribble et al., Heterocycles, vol. 35 (1993), pp. 151–169, "Regioselective ortho–lithiation of halopyridines . . . ".

Effenberger et al., Chem. Ber., vol. 124 (1991), pp. 2119–2125, "Darstellung van didehydropyridinen aus (trimethylsilyl)pyridinen".

Miki et al., Heterocycles, vol. 48 (1998), pp. 1593–1597. "Reaction of 1–benzylindole–2,3–dicarboxylic anhydride with 3–bromo–4–lithiopyridine . . . ".

*Primary Examiner*—Venkataraman Balasubramanian
(74) *Attorney, Agent, or Firm*—Baerbel R. Brown; Melvin Winokur

(57) ABSTRACT

The present invention is directed to radiolabeled neuropeptide Y Y5 receptor antagonists which are useful for the labeling and diagnostic imaging of neuropeptide Y Y5 receptors in mammals.

10 Claims, No Drawings

RADIOLABELED NEUROPEPTIDE Y Y5 RECEPTOR ANTAGONISTS

CROSS-REFERENCE TO RELATED APPLICATIONS

This application is a U.S. National Phase application under 35 U.S.C. §371 of PCT Application No. PCT/US02/23044, filed Jul. 19. 2002. which claims priority under 35 U.S.C. §119 from U.S. provisional application Ser. No. 60/307,499, filed Jul. 24, 2001.

BACKGROUND OF THE INVENTION

Noninvasive, nuclear imaging techniques can be used to obtain basic and diagnostic information about the physiology and biochemistry of a variety of living subjects including experimental animals, normal humans and patients. These techniques rely on the use of sophisticated imaging instrumentation which is capable of detecting radiation emitted from radiotracers administered to such living subjects. The information obtained can be reconstructed to provide planar and tomographic images which reveal distribution of the radiotracer as a function of time. Use of appropriately designed radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the subject or the effects that various diseases or drugs have on the physiology or biochemistry of the subject. Currently, radiotracers are available for obtaining useful information concerning such things as cardiac function, myocardial blood flow, lung perfusion, liver function, brain blood flow, regional brain glucose and oxygen metabolism.

Compounds can be labeled with either positron or gamma emitting radionuclides. For imaging, the most commonly used positron emitting (ET) radionuclides are $^{11}C$, $^{18}F$, $^{15}O$ and $^{13}N$, all of which are accelerator produced, and have half-lives of 20, 110, 2 and 10 min. respectively. Since the half-lives of these radionuclides are so short, it is only feasible to use them at institutions which have an accelerator on site for their production, thus limiting their use. Given the recent increase in the number of cyclotrons, the positron emitting radionuclide, $^{18}F$, is now widely available so that $^{18}F$ labeled radiotracers are now available to most hospitals in the U.S. and much of the rest of the world. Several gamma-emitting radiotracers are available which can be used by essentially any hospital in the U.S. and in most hospitals worldwide. The most widely used of these are $^{99m}Tc$, $^{201}Tl$ and $^{123}I$.

In the past two decades, one of the most active areas of nuclear medicine research has been the development of receptor imaging radiotracers. These tracers bind with high affinity and specificity to selective hormone receptors and neuroreceptors. Successful examples include radiotracers for imaging the following receptor systems: estrogen, muscarinic, dopamine D1 and D2, and opiate.

Neuropeptide Y (NPY) is a 36 amino acid peptide that is a member of the pancreatic polypeptide family, which also includes pancreatic polypeptide (PP) and peptide YY (PYY). NPY is located throughout the central and peripheral nervous systems and affects a diverse range of biological functions, including central endocrine secretion, vascular and smooth muscle activity, appetite, memory, anxiety, blood pressure regulation and reproduction. See, e.g., Karla, et al., *Phys. & Behavior* 50, 5 (1991).

NPY receptors are members of the G protein-coupled receptor superfamily. At present, NPY is known to bind to at least five receptors: Y1, Y2, Y3, Y4 and Y5. NPY Y5 agonists and antagonists are being developed for the treatment of physiological disorders associated with an imbalance of NPY Y5, i.e., as a treatment for obesity, diabetes, anorexia and bulimia.

PET (Positron Emission Tomography) radiotracers and imaging technology may provide a powerful method for clinical evaluation and dose selection of neuropeptide Y Y5 receptor antagonists. Using a fluorine-18 or carbon-11 labeled radiotracer that provides a neuropeptide Y Y5 receptor-specific image in the brain and other tissues, the dose required to saturate neuropeptide Y Y5 receptors can be determined by the blockade of the PET radiotracer image in humans. The rationale for this approach is as follows: efficacy of a neuropeptide Y Y5 receptor antagonist is a consequence of the extent of receptor inhibition, which in turn is a function of the degree of drug-receptor occupancy.

It is, therefore, an object of this invention to develop radiolabeled neuropeptide Y Y5 receptor antagonists that would be useful not only in traditional exploratory and diagnostic imaging applications, but would also be useful in assays, both in vitro and in vivo, for labeling the neuropeptide Y Y5 receptor and for competing with unlabeled neuropeptide Y Y5 receptor antagonists and agonists. It is a further object of this invention to develop novel assays which comprise such radiolabeled compounds.

SUMMARY OF THE INVENTION

The present invention is directed to certain radiolabeled neuropeptide Y Y5 receptor antagonists. The present invention is further concerned with methods for the use of such radiolabeled neuropeptide Y Y5 receptor antagonists for the labeling and diagnostic imaging of neuropeptide Y Y5 receptors in mammals.

DETAILED DESCRIPTION OF THE INVENTION

The present invention is directed to certain radiolabeled neuropeptide Y Y5 receptor antagonists. In particular, the present invention is directed to a compound of the formula:

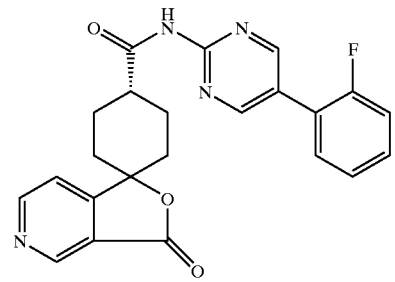

which can be labeled with a radionuclide selected from the group consisting of: $^{3}H$, $^{11}C$, $^{18}F$, $^{15}O$ and $^{13}N$. In addition, analogs of this compound could be labeled with $^{125}I$, $^{123}I$, $^{131}I$, $^{75}Br$, $^{15}O$, $^{13}N$, $^{211}At$, $^{82}Br$, $^{77}Br$ or $^{76}Br$.

In a preferred embodiment of the present invention the radionuclide is selected from the group consisting of $^{11}C$ or $^{18}F$.

The present invention is also directed to a radiopharmaceutical composition which comprises a compound of the present invention and at least one pharmaceutically acceptable carrier or excipient.

The present invention is also directed to a method for labeling neuropeptide Y Y5 receptors in a mammal which comprises administering to a mammal in need of such labeling an effective amount of the radiolabeled compound of the present invention.

The present invention is also directed to a method for diagnostic imaging of neuropeptide Y Y5 receptors in a mammal which comprises administering to a mammal in need of such diagnostic imaging an effective amount of the radiolabeled compound of the present invention.

The present invention is also directed to a method for diagnostic imaging of tissues bearing neuropeptide Y Y5 receptors in a mammal which comprises administering to a mammal in need of such diagnostic imaging an effective amount of the radiolabeled compound of the present invention.

The present invention is also directed to a method for the diagnostic imaging of neuropeptide Y Y5 binding sites in tissues of a mammalian species which comprises administering to the mammalian species in need of such diagnostic imaging an effective amount of the radiolabeled compound of the present invention.

The present invention is also directed to a method for diagnostic imaging of the brain in a mammal which comprises administering to a mammal in need of such diagnostic imaging an effective amount of the radiolabeled compound of the present invention.

The present invention is further directed to a method for the detection or quantification of neuropeptide Y Y5 receptors in mammalian tissue which comprises administering to a mammal in which such quantification is desired an effective amount of the radiolabeled compound of the present invention.

In a preferred embodiment of the methods of the present invention, the mammal is a human.

The present invention is further directed to a process for the preparation of [$^{11}$C]trans-N-[5-(2-fluorophenyl)-2-pyrimidinyl]-3-oxospiro[5-azaisobenzofurane-1(3H),1'-cyclohexane]-4'-carboxamide.

Suitable radionuclides that may be incorporated in the instant compounds include $^3$H (also written as T), $^{11}$C, $^{18}$F, $^{125}$I, $^{82}$Br, $^{123}$I, $^{131}$I, $^{75}$Br, $^{15}$O, $^{13}$N, $^{211}$At or $^{77}$Br. The radionuclide that is incorporated in the instant radiolabeled compounds will depend on the specific analytical or pharmaceutical application of that radiolabeled compound. Thus, for in vitro labeling of neuropeptide Y Y5 receptors and competition assays, compounds that incorporate $^3$H, $^{125}$I or $^{82}$Br will generally be most useful. For diagnostic imaging agents, compounds that incorporate a radionuclide selected from $^{11}$C, $^{18}$F, $^{123}$I, $^{131}$I, $^{75}$Br, $^{76}$Br or $^{77}$Br are preferred. In certain applications incorporation of a chelating radionuclide such as Tc$^{99m}$ may also be useful.

Radiolabeled neuropeptide Y Y5 receptor antagonists, when labeled with the appropriate radionuclide, are potentially useful for diagnostic imaging, basic research, and radiotherapeutic applications. Specific examples of possible diagnostic imaging and radiotherapeutic applications, include determining the location, the relative activity and/or the abundance of neuropeptide Y Y5 receptors, radioimmunoassay of neuropeptide Y Y5 receptor antagonists, and autoradiography to determine the distribution of neuropeptide Y Y5 receptors in a mammal or an organ or tissue sample thereof.

In particular, the instant radiolabeled neuropeptide Y Y5 receptor antagonists when labeled with the positron emitting radionuclide, F-18, are useful for positron emission tomographic (PET) imaging of neuropeptide Y Y5 receptors in the brain of living humans and experimental animals. This radiolabeled neuropeptide Y Y5 receptor antagonists may be used as research tools to study the interaction of unlabeled neuropeptide Y Y5 antagonist with neuropeptide Y Y5 receptors in vivo via competition between the labeled drug and the radiolabeled compound for binding to the receptor. This type of study is useful for determining the relationship between neuropeptide Y Y5 receptor occupancy and dose of unlabeled neuropeptide Y Y5 receptor antagonist, as well as for studying the duration of blockade of the receptor by various doses of the unlabeled neuropeptide Y Y5 receptor antagonist. As a clinical tool, the radiolabeled neuropeptide Y Y5 receptor antagonists may be used to help define a clinically efficacious dose of a neuropeptide Y Y5 receptor antagonist. In animal experiments, the radiolabeled neuropeptide Y Y5 receptor antagonists can be used to provide information that is useful for choosing between potential drug candidate for selection for clinical development. The radiolabeled neuropeptide Y Y5 receptor antagonists may also be used to study the regional distribution and concentration of neuropeptide Y Y5 receptors in the living human brain, as well as the brain of living experimental animals and in tissue samples. The radiolabeled neuropeptide Y Y5 receptor antagonists may also be used to study disease or pharmacologically related changes in neuropeptide Y Y5 receptor concentrations.

For example, a positron emission tomography (PET) tracer such as the present radiolabeled neuropeptide Y Y5 receptor antagonists which can be used with currently available PET technology to obtain the following information: relationship between level of receptor occupancy by candidate neuropeptide Y Y5 antagonist and clinical efficacy in patients; dose selection for clinical trials of neuropeptide Y Y5 antagonists prior to initiation of long term clinical studies; comparative potencies of structurally novel neuropeptide Y Y5 antagonists; investigating the influence of neuropeptide Y Y5 antagonists on in vivo receptor affinity and density during the treatment of clinical targets with neuropeptide Y Y5 receptor antagonists and other agents; changes in the density and distribution of neuropeptide Y Y5 receptors during e.g. psychiatric diseases in their active stages, during effective and ineffective treatment and during remission; and changes in neuropeptide Y Y5 receptor expression and distribution in CNS disorders (e.g. depression, head injury and Parkinson's disease).

For the use of the instant compounds as exploratory or diagnostic imaging agents, the radiolabeled compounds may be administered to mammals, preferably humans, in a pharmaceutical composition, either alone or, preferably, in combination with pharmaceutically acceptable carriers or diluents, optionally with known adjuvants, such as alum, in a pharmaceutical composition, according to standard pharmaceutical practice. Such compositions can be administered orally or parenterally, including the intravenous, intramuscular, intraperitoneal, subcutaneous, rectal and topical routes of administration. Preferably, administration is intravenous.

Radiotracers labeled with short-lived, positron-emitting radionuclides are almost always administered via intravenous injection within less than one hour of their synthesis. This is necessary because of the short half-life of the radionuclides involved (20 and 110 minutes for C-11 and F-18 respectively).

A minimum dosage level for the labeled neuropeptide Y Y5 receptor antagonist is about 1 mCi to about 10 mCi.

More particularly, a dosage level for the labeled neuropeptide Y Y5 receptor antagonist is about 5 mCi to about 10 mCi. It will be appreciated that the amount of the neuropeptide Y Y5 receptor antagonist required for use in the present invention will vary not only with the particular compounds or compositions selected but also with the route of administration, the nature of the condition being treated or studied, and the age and condition of the patient, and will ultimately be at the discretion of the patient's physician or pharmacist. The dosage to be used will be that which provides sufficient concentration of radioactivity in the brain to permit acquisition of good brain images between 30 and 240 min after administration.

When a radiolabeled neuropeptide Y Y5 receptor antagonist according to this invention is administered into a human subject, the amount required for diagnostic imaging will normally be determined by the prescribing physician with the dosage generally varying according to the age, weight, and response of the individual patient, as well as the quantity of emission from the radionuclide. However, in most instances, an effective amount will be the amount of compound sufficient to produce good images and should be in the range of from about 5 to 10 mCi.

In one exemplary application, administration occurs in an amount of radiolabeled compound of between about 0.005 $\mu$g/kg of body weight to about 50 $\mu$g/kg of body weight per day, preferably of between 0.02 $\mu$g/kg of body weight to about 3 $\mu$g/kg of body weight. A particular analytical dosage that comprises the instant composition includes from about 0.5 $\mu$g to about 100 $\mu$g of a labeled neuropeptide Y Y5 receptor antagonist. Preferably, the dosage comprises from about 1 $\mu$g to about 50 $\mu$g of a radiolabeled neuropeptide Y Y5 receptor antagonist.

The following illustrative procedure may be utilized when performing PET imaging studies on patients in the clinic. A 20 G two inch venous catheter is inserted into the contralateral ulnar vein for radiotracer administration. The patient is positioned in the PET camera and a tracer dose of [$^{15}$O]H$_2$O administered via i.v. catheter. The image thus obtained is used to insure that the patient is positioned correctly to include the brain or other areas of interest. Subsequently the [$^{11}$C] neuropeptide Y Y5 receptor antagonist (<20 mCi) is administered via i.v. catheter. Following the acquisition of the total radiotracer image, an infusion is begun of the neuropeptide Y Y5 receptor antagonist which is being clinically evaluated at one of three dose rates (0.1, 1 or 10 mpk/day). After infusion for 2.5 hrs, the [$^{11}$C] neuropeptide Y Y5 receptor antagonist is again injected via the catheter. Alternatively, the neuropeptide Y Y5 antagonist can be administered orally and the tracer injected about 2–2.5 hours later and again at any time of interest after dosing with the unlabeled antagonist. Images are acquired for up to 90 min. Within ten minutes of the injection of radiotracer and at the end of the imaging session, 1 ml blood samples are obtained for determining the plasma concentration of the clinical candidate.

For determining the distribution of radiotracer, regions of interest (ROIs) are drawn on the reconstructed image including, e.g. the brain and the central nervous system. These regions are used to generate time activity curves obtained in the absence of receptor antagonist or in the presence of the clinical candidate at the various infusion doses examined. Data are expressed as radioactivity per unit time per unit volume ($\mu$Ci/cc/mCi injected dose). Inhibition curves are generated from the data obtained in a region of interest obtained starting at 70 minutes post-injection of radiotracer. At this time, clearance of non-specific binding has reached steady state. The ID$_{50}$ values are obtained by curve fitting the dose-rate/inhibition curves with equation iii:

$$B = A_0 - A_0 * I/(ID_{50}+I) + NS \qquad (iii)$$

where B is the %-Dose/g of radiotracer in tissues for each dose of clinical candidate, A$_0$ is the specifically bound radiotracer in a tissue in the absence of a neuropeptide Y Y5 receptor antagonist, I is the injected dose of antagonist, ID$_{50}$ is the dose of compound which inhibits 50% of specific radiotracer binding to a neuropeptide Y Y5 receptor, and NS is the amount of non-specifically bond radiotracer.

PET Imaging in Monkey

Male rhesus monkeys weighing 7–11 kg are fasted for at least 12 hours allowing water intake ad libitum. A 20 G two inch venous catheter is placed into the saphenous vein through which anesthesia is introduced by propofol 5 mg/kg in~3 ml and maintained with additional propofol at an average dose of 0.4 mg/kg/h. Another catheter is inserted into the contralateral saphenous vein for radiotracer administration.

Oxygen saturation of circulating blood is measured with a pulse oximeter (Nellcor Inc., Hayward, Calif.) placed on the finger of the animal. Circulatory volume is maintained by intravenous infusion of isotonic saline. Heart rate, and core temperature are monitored continuously.

The animal is positioned in the PET camera and a tracer dose of [$^{15}$O]H$_2$O administered via i.v. catheter. The image thus obtained is used to insure that the monkey is positioned correctly to include the brain and other areas of interest. Subsequently [$^{11}$C]-neuropeptide Y Y5 receptor antagonist (<20 mCi) is administered via i.v. catheter. Following the acquisition of the total radiotracer image, an infusion is begun of the unlabeled neuropeptide Y Y5 receptor antagonist at one of three dose rates (0.1, 1 or 10 mpk/day). After infusion for 2.5 hrs, [$^{11}$C]-neuropeptide Y Y5 receptor antagonist is again injected via the catheter. Images are again acquired for up to 90 min. Within ten minutes of the injection of radiotracer and at the end of the imaging session, 1 ml blood samples are obtained for determining the plasma concentration of test compound. In one imaging session, a dose of 10 mpk of another neuropeptide Y Y5 receptor antagonist is infused over 5 minutes. This dose has been determined to completely block radiotracer binding and thus is used to determine the maximum receptor-specific signal obtained with the PET radiotracer. At the conclusion of the study, animals are recovered and returned to animal housing.

For uninhibited distribution of radiotracer, regions of interest (ROIs) are drawn on the reconstructed image including the brain. These regions are used to generate time activity curves obtained in the absence of test compound or in the presence of test compound at the various infusion doses examined. Data are expressed as radioactivity per unit time per unit volume ($\mu$Ci/cc/mCi injected dose). Inhibition curves are generated from the data obtained in a region of interest obtained starting at 70 min. post-injection of radiotracer. By this time, clearance of non-specific binding will have reached steady state. The ID$_{50}$ are obtained by curve fitting the dose-rate/inhibition curves with equation iii, hereinabove.

Neuropeptide Y Y5 receptor antagonists which incorporate a radionuclide may be prepared by first synthesizing an unlabeled compound that optionally incorporates an iodo or bromo moiety and then exchanging the halogen moiety with an appropriate radionuclide using techniques well known in the art. Alternately, a radiolabeled neuropeptide Y Y5 receptor antagonist may be prepared by alkylation with a radiolabeled alkylating agent. Syntheses of unlabeled neuropeptide Y Y5 receptor antagonist have been generally described in various patents and publications. Syntheses of particular neuropeptide Y Y5 receptor antagonists is described below.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

In particular, amino moieties may be protected by, for example, the formation of alkoxycarbonyl derivatives, e.g. tert-butoxycarbonyl and trichloroethoxycarbonyl, or benzyl, trityl or benzyloxycarbonyl derivatives. Subsequent removal of the protecting group is achieved by conventional procedures thus, for example, tert-butoxycarbonyl, benzyl or benzyloxycarbonyl groups may be removed by hydrogenolysis in the presence of a catalyst e.g. palladium; a trichloroethoxycarbonyl group may be removed with zinc dust; and a trityl group may be removed under acidic conditions using standard procedures.

Where hydroxyl groups require protection, this may be effected by the formation of esters or trialkylsilyl, tetrahydropyran or benzyl ethers. Such derivatives may be deprotected by standard procedures thus, for example, a tetrahydropyran ether derivative may be deprotected using hydrochloric acid in methanol.

In some cases the order of carrying out the following reaction schemes may be varied to facilitate the reaction or to avoid unwanted reaction products.

The following examples are provided for the purpose of further illustration only and are not intended to be limitations on the disclosed invention.

In the schemes and examples below, various reagent symbols and abbreviations have the following meanings:
EtOAc Ethyl acetate
CHCl₃ Chloroform
DMC 2-Chloro-1,3-diethyl-2-imidazolinium chloride
DME 1,2-Dimethoxyethane
Et₃N Triethylamine
Et₄NCN Tetraethylammonium cyanide
H₂SO₄ Sulfuric acid
IPE Diisopropyl ether
K₂CO₃ Potassium carbonate
LDA Lithium diisopropylamide
MsCl Methanesulfonyl chloride
MTBE tert-Butyl methyl ether
NaBH₄ Sodium borohydride
NaHCO₃ Sodium bicarbonate
Pd(PPh₃)₄ Tetrakis(triphenylphosphine)palladium(0)
THF Tetrahydrofuran
p-TsOH p-Toluenesulfonic acid

SCHEME I

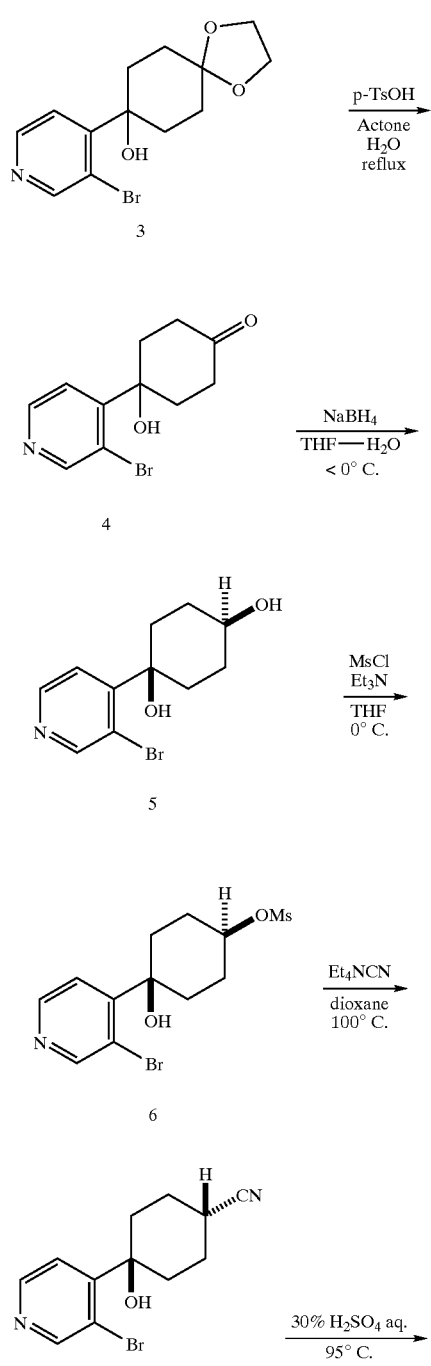

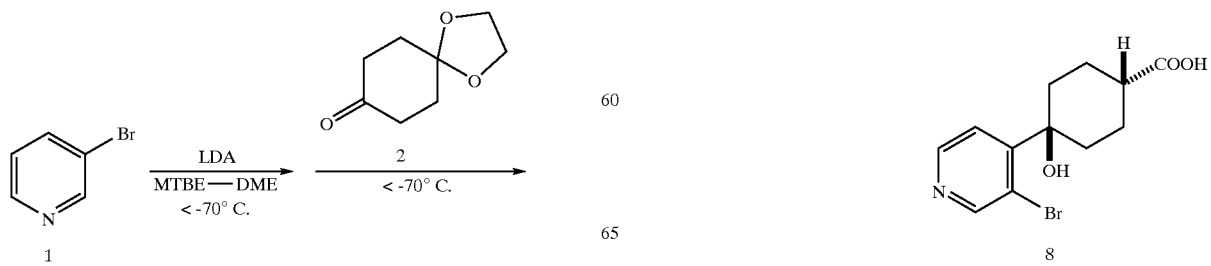

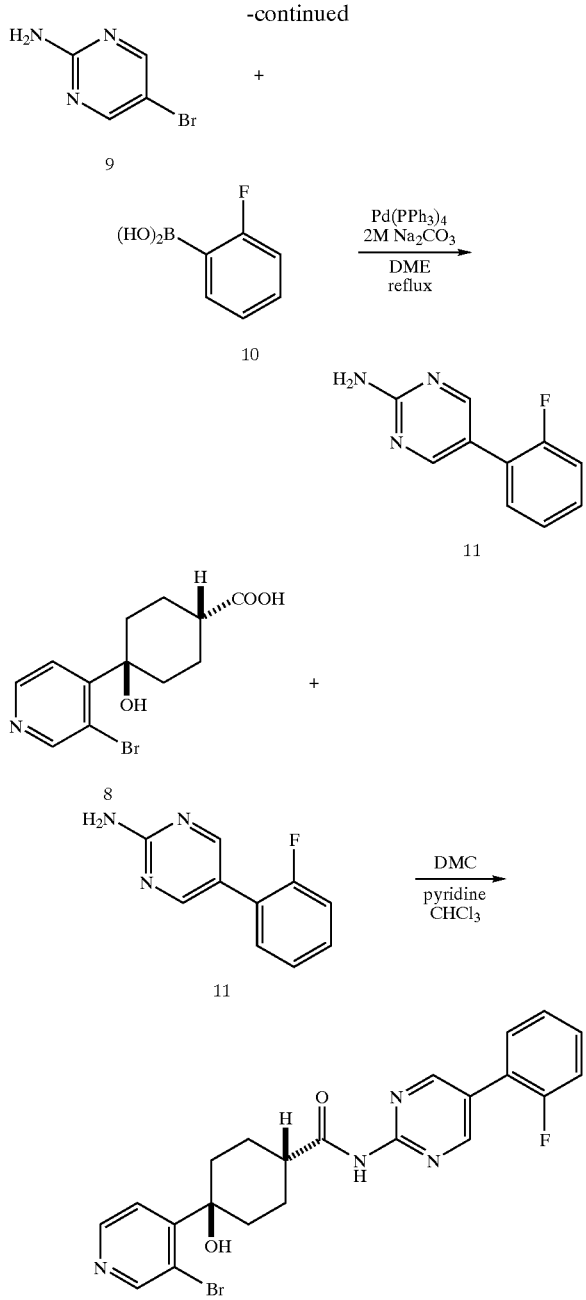

EXAMPLE 1
Synthesis of Ketal (3)

n-Butyllithium (1.59 M in hexane, 210 mL, 334 mmol) was added to a solution of diisopropylamine (49 mL, 349 mmol) in anhydrous tert-butylmethylether (1000 mL) and anhydrous dimethoxyethane (200 mL) below −35° C. under nitrogen atmosphere. After 30 min., the solution was cooled at −74° C. and 3-bromopyridine 1 (30.5 mL, 317 mmol) was added to the mixture below −70° C. To the mixture was added dropwise a solution of 1,4-cyclohexanedione monoethylene ketal 2 (49.44 g, 316 mmol) in anhydrous tetrahydrofuran (100 mL) below −64° C. After stirring for 15 min., saturated NH$_4$Cl (800 mL) was added to the reaction mixture. The mixture was allowed to warm to room temperature, and water (300 mL) and EtOAc (500 mL) were added. The organic layer was separated and washed with brine. The aqueous layer was extracted with EtOAc (1000 mL) and washed with brine. The combined organic layers were dried over Na$_2$SO$_4$ and concentrated in vacuo. The residual solid was triturated with EtOAc (300 mL) and IPE (500 mL). The precipitate was collected by filtration to afford the title compound 3 as crystals. The filtrate was concentrated in vacuo and the residue diluted with IPE and a slight amount of the seed was added. The solution was stirred for 6.5 hr. and the precipitate was collected by filtration to afford the title compound 3 as crystals.

EXAMPLE 2
Synthesis of Ketone (4)

p-Toluenesulfonic acid mono hydrate (5.64 g, 29.6 mmol) was added to a solution of ketal 3 (46.59 g, 148 mmol) in acetone (465 mL) and water (465 mL) at room temperature. The mixture was stirred under reflux overnight, acetone was removed by distillation, and the solution was poured into saturated NaHCO$_3$ (100 mL). The mixture was extracted with CHCl$_3$ (500 mL×3,300 mL×1). The combined organic layers were dried over magnesium sulfate and concentrated in vacuo. The residual solid was triturated with CHCl$_3$ (50 mL) and IPE (300 mL). The precipitate was collected by filtration to afford the title compound 4 as crystals.

EXAMPLE 3
Synthesis of Alcohol (5)

Sodium borohydride (1.68 g, 44.4 mmol) was slowly added to a solution of ketone 4 (38.9 g, 144 mmol) in tetrahydrofuran (390 mL) and water (390 mL) at 0° C. The mixture was stirred at 0° C. for 60 min. and quenched with saturated NH$_4$Cl (100 mL). The mixture was extracted with CHCl$_3$/EtOH (7/1, 800 mL×2, 5/1,500 mL×2) solution. The organic layer was dried over Na$_2$SO$_4$ and concentrated in vacuo. The residue was triturated with CHCl$_3$ and the precipitate was collected by filtration to afford the title compound 5 as crystals.

EXAMPLE 4
Synthesis of Mesylate (6)

Triethylamine (25 mL, 179 mmol) and methanesulfonyl chloride (11.7 mL, 151 mmol) were added to a suspension of alcohol 5 (34.27 g, 126 mmol) in anhydrous tetrahydrofuran (650 mL) at 0° C. under a nitrogen atmosphere. The suspension was stirred at 0° C. for 30 min., diluted with EtOAc (650 mL) and quenched with saturated NH$_4$Cl (300 mL). The organic layer was separated and the aqueous layer was extracted with EtOAc (300 mL×2). The organic layer was washed with brine, dried over Na$_2$SO$_4$ and concentrated in vacuo. The residual solid was washed with IPE to afford the mesylate 6 as crystals.

EXAMPLE 5
Synthesis of Nitrile (7)

Tetraethylammonium cyanide (49.85 g, 319 mmol) was added to a solution of mesylate 6 (43.72 g, 124 mmol) in anhydrous 1,4-dioxane (450 mL) at room temperature. The mixture was stirred at 100° C. overnight, cooled to room temperature, poured into water (450 mL), and extracted with EtOAc (900 mL×3). The organic layer was washed with water (100 mL) and brine (100 mL), dried over Na$_2$SO$_4$, and concentrated in vacuo. The residual solid was purified by column chromatography on silica gel (hexane:acetone=2:1). The obtained solid was washed with IPE to afford the title compound 7 as a white solid.

EXAMPLE 6
Synthesis of Carboxylic Acid (8)

A solution of conc. sulfuric acid (75 mL) and water (175 mL) was added to nitrile 7 (24.23 g, 86.2 mmol) at room temperature. The mixture was stirred at 95° C. for 2 days, cooled to room temperature, poured into water (500 mL), and added to K$_2$CO$_3$ (200 g). The suspension was extracted with EtOAc (1000 mL, 500 mL×2). The combined organic layers were dried over Na$_2$SO$_4$, and concentrated in vacuo. The precipitate was collected by filtration to afford the EtOAc adduct of the title compound 8 as crystals. The suspension of the crystals of the EtOAc adduct of 8 in IPE (270 mL) was stirred for 3 hr, then collected by filtration to afford the title compound 8 as a white solid.

EXAMPLE 7
Synthesis of 2-Amino-5-(2-fluorophenyl)-pyrimidine (11)

To a solution of 2-amino-5-bromo-pyrimidine 9 (49.40 g, 284 mmol) in dimethoxyethane (500 mL) were added 2-fluorophenylboronic acid 10 (43.66 g, 312 mmol), 2.0 M aqueous sodium carbonate solution (285 mL, 570 mmol) and tetrakis(triphenylphosphine)palladium (0) (3.28 g, 2.84 mmol). The mixture was stirred at reflux for 2 hr. The reaction mixture was cooled to ambient temperature and slowly poured into 10% H$_2$SO$_4$ (600 mL), which was added with hexane (300 mL). The acidic aqueous layer was separated, and the insoluble material and the organic layer was extracted with 10% H$_2$SO$_4$ (200 mL×2). The combined acidic aqueous layers were washed with EtOAc (200 mL), neutralized with K$_2$CO$_3$ to give a precipitate of the title compound and an inorganic salt, which were washed with water (3000 mL) to afford the title compound 11 as a white solid. The white solid was dissolved in hot THF (500 mL). The insoluble material was filtered off and concentrated in vacuo. The residual solid was washed with IPE to afford the title compound 11 as crystals.

EXAMPLE 8
Synthesis of trans-4-(3-bromopyridin-4-yl)-4-hydroxy-N-[5-(2-fluorophenyl)-2-pyrimidinyl]-cyclohexanecarboxamide 2-chloro-1,3-dimethyl-2-imidazolinium chloride (14.16 g, 83.76 mmol) was added to a mixture of carboxylic acid 8 (23.00 g, 76.63 mmol) and 2-amino-5-(2-fluorophenyl)pyrimidine 11 (13.21 g, 69.82 mmol) in chloroform (114 mL) and pyridine (114 mL), and the mixture was stirred for 3 days. The reaction mixture was diluted with ethyl acetate (800 mL) and THF (100 mL), and washed with 10% citric acid (800 mL), sat. NaHCO$_3$ (200 mL) and brine (100 mL). The aqueous layer was extracted with EtOAc (500 mL) and THF (100 mL) three times, washed with water (200 mL), sat. NaHCO$_3$ (100 mL) and brine (100 mL). The combined organic layers were dried over Na$_2$SO$_4$ and concentrated in vacuo. The residue was purified by chromatography on silica gel (EtOAc—methanol/CHCl$_3$=1/15), and crystallized from EtOAc to afford the title compound as a slightly brown powder.

EXAMPLE 9
Purification of trans-4-(3-bromopyridin-4-yl)-4-hydroxy-N-[5-(2-fluorophenyl)-2-pyrimidinyl]-cyclohexanecarboxamide Trans-4-(3-bromopyridin-4-yl)-4-hydroxy-N-[5-(2-fluorophenyl)-2-pyrimidinyl]-cyclohexanecarboxamide was dissolved in THF (94 mL). tert-Butylmethylether (470 mL) was slowly added to the solution with stirring. The precipitate was collected by filtration to afford the title compound as a slightly brown solid.

Trans-4-(3-bromopyridin-4-yl)-4-hydroxy-N-[5-(2-fluorophenyl)-2-pyrimidinyl]-cyclohexanecarboxamide was dissolved in chloroform (156 mL) and activated carbon (1.61 g) was added to the solution. The mixture was stirred for 30 min. and the activated carbon was filtered off. The solution was concentrated in vacuo and EtOAc (153 mL) was added. The solution was stirred, the precipitate gradually appeared, and was collected by filtration to afford the title compound. It was dissolved in THF (300 mL) and concentrated in vacuo. The oily residue was diluted with THF (70 mL) and tert-butylmethylether (425 mL) was slowly added with stirring. The precipitate was collected by filtration to afford the title compound as a white solid.

$^1$H NMR (300 MHz, DMSO-d6): d 1.49–1.57 (m, 2 H), 1.78–1.88 (m, 2 H), 1.97–2.08 (m, 2 H), 2.62–2.72 (m, 2 H), 2.87–2.93 (m, 1H), 7.32–7.39 (m, 2 H), 7.44–7.50 (m, 1 H), 7.63–7.70 (m, 2 H), 8.48 (d, 2 H, J=5.3 Hz), 8.62 (s, 1 H), 8.84 (s, 2 H), 10.60 (s, 1 H). ESI-Mass: m/e 471, 473 (M+H)$^+$

EXAMPLE 10
[$^{11}$C]trans-N-[5-(2-fluorophenyl)-2-pyrimidinyl]-3-oxospiro[5-azaisobenzofurane-1(3H),1'-cyclohexane]-4'-carboxamide

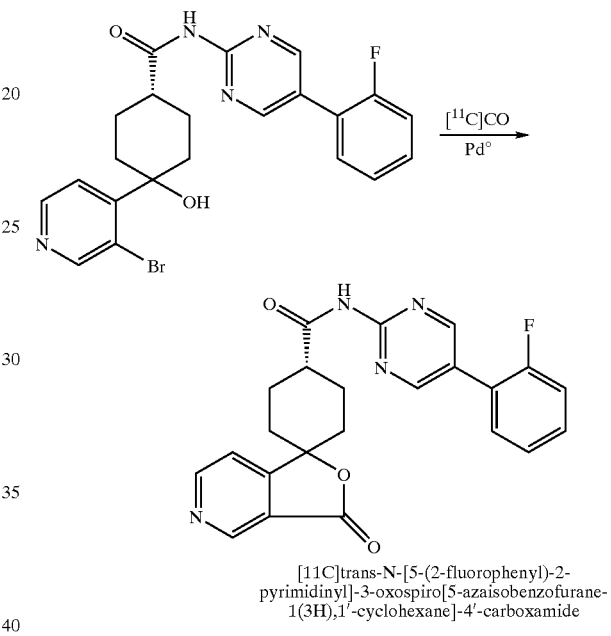

[11C]trans-N-[5-(2-fluorophenyl)-2-pyrimidinyl]-3-oxospiro[5-azaisobenzofurane-1(3H),1'-cyclohexane]-4'-carboxamide

[$^{11}$C]Carbon dioxide production is performed using a Scanditronix MC-17 cyclotron at the Uppsala University PET Center. The $^{14}$N(p,α)$^{11}$C reaction is employed in a gas target containing nitrogen (AGA, Nitrogen 6.0) and 0.1% oxygen (AGA, Oxygen 4.8), which is bombarded with 17 MeV protons. [$^{11}$C]Carbon dioxide is reduced to [$^{11}$C] carbon monoxide in a small zinc filled tube (85×2 mm, 0.65 g of Zn) at 400° C.

A 1 mL vial is charged with trans-4-(3-bromopyridin-4-yl)-4-hydroxy-N-[5-(2-fluorophenyl)-2-pyrimidinyl]-cyclohexanecarboxamide (0.5 mg) and Pd(PPh$_3$)$_4$ (1.2–1.4 mg) in THF (0.3 mL). The vial is capped, flushed with nitrogen and shaken until homogeneous. After 25 minutes at room temperature, the mixture is transferred with pressure (35 Mpa) to the micro-autoclave precharged with [$^{11}$C] carbon monoxide. The micro-autoclave is heated (125° C.) at 5000 psi for 5 minutes. The reactor is then emptied into a 1.8 ml glass-vial and 1.5 ml of water is added to the approx. 0.25 ml of THF. This solution is then injected directly onto the preparative LC (Genesis C18, 10×250 mm, 5 mL/min, 35% water/acetonitrile (7/50):ammonium formate (50 mM, pH 3.5) to 70% water/acetonitrile (7/50) :ammonium formate (50 mM, pH 3.5) over 6 minutes, hold at 70% for 12 minutes). The retention-time of the product is 9.2 minutes. The product peak is collected and the eluent was removed under vacuum. A solution of 30% propyleneglycol ether/10% ethanol in water is added and the resulting solution was passed through a sterile filter (0.22 um) into a septum equipped sterile vial.

As an alternative approach, the 5-azaisobenzofurane ring may also be synthesized from the corresponding 3-iodopyridine precursor as shown in Scheme II. Additionally, other 3-substituted pyridine precursors with leaving groups, such as, but not limited to, triflate, chloride, and fluoride, in the 3 position may also be employed. Other leaving groups which may be used in the present invention include, but are not limited to, those described in F. A. Carey and R. J. Sundberg, *Advanced Organic Chemistry,* Part A, Kluwer Academic/Plenum Publishers, 2000; and M. B. Smith and J. March, *March's Advanced Organic Chemistry,* John Wiley & Sons, 2001.

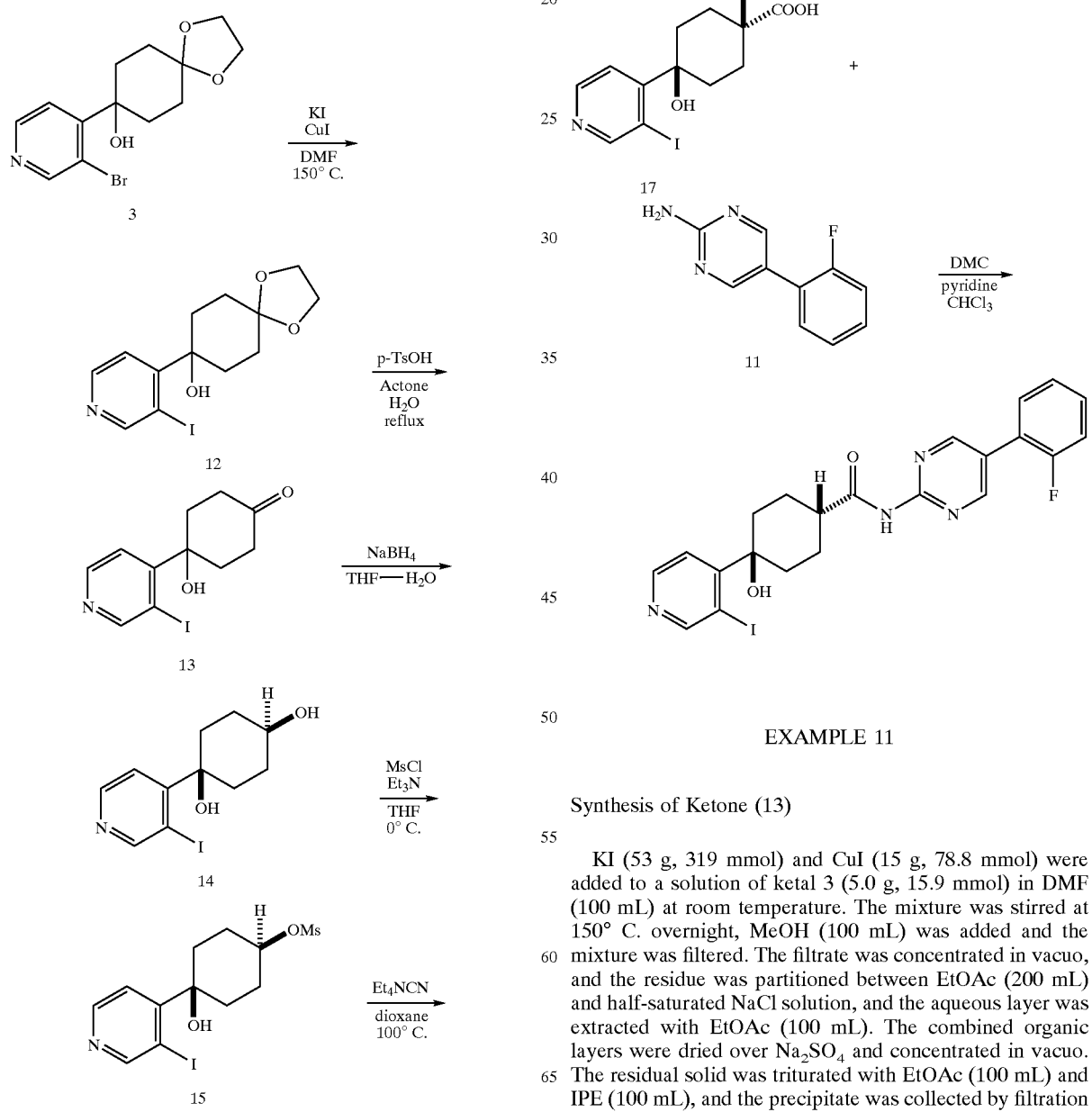

EXAMPLE 11

Synthesis of Ketone (13)

KI (53 g, 319 mmol) and CuI (15 g, 78.8 mmol) were added to a solution of ketal 3 (5.0 g, 15.9 mmol) in DMF (100 mL) at room temperature. The mixture was stirred at 150° C. overnight, MeOH (100 mL) was added and the mixture was filtered. The filtrate was concentrated in vacuo, and the residue was partitioned between EtOAc (200 mL) and half-saturated NaCl solution, and the aqueous layer was extracted with EtOAc (100 mL). The combined organic layers were dried over $Na_2SO_4$ and concentrated in vacuo. The residual solid was triturated with EtOAc (100 mL) and IPE (100 mL), and the precipitate was collected by filtration to afford the iodide 12 as a solid.

The iodide 12 (7.84 g) was dissolved in acetone (70 mL) and water (70 mL), and p-toluenesulfonic acid mono hydrate (0.60 g, 3.15 mmol) was added to the solution. The mixture was stirred under reflux for 6 h, acetone was removed by distillation, and the solution was poured into saturated NaHCO$_3$ (10 mL). The mixture was extracted with CHCl$_3$ (50 mL×5). The combined organic layers were dried over Na$_2$SO$_4$ and concentrated in vacuo. The residual solid was triturated with IPE (100 mL), and the precipitate was collected by filtration to afford the title compound 13 as a solid.

EXAMPLE 12
Synthesis of Alcohol (14)

Sodium borohydride (150 mg, 3.97 mmol) was slowly added to a solution of ketone 13 (3.0 g, 9.46 mmol) in tetrahydrofuran (14 mL) and water (14 mL) at 0° C. The mixture was stirred at 0° C. for 1.5 h and quenched with saturated NH$_4$Cl (60 mL). The mixture was extracted with EtOAc (300 mL+100 mL). The combined organic layers were dried over Na$_2$SO$_4$ and concentrated in vacuo. The residue was triturated with CHCl$_3$ and the precipitate was collected by filtration to afford the title compound 14 as a solid.

EXAMPLE 13
Synthesis of Mesylate (15)

Triethylamine (1.4 mL, 10.0 mmol) and methanesulfonyl chloride (0.63 mL, 8.14 mmol) were added to a suspension of alcohol 14 (2.0 g, 6.27 mmol) in anhydrous tetrahydrofuran (40 mL) at 0° C. under a nitrogen atmosphere. The suspension was stirred at 0° C. for 1 h, diluted with EtOAc (100 mL) and washed with water and brine, dried over Na$_2$SO$_4$ and concentrated in vacuo to afford the mesylate 15 as a foam.

EXAMPLE 14
Synthesis of Nitrile (16)

Tetraethylammonium cyanide (2.5 g, 16.0 mmol) was added to a solution of mesylate 7 (2.49 g, 6.27 mmol) in anhydrous 1,4-dioxane (30 mL) at room temperature. The mixture was stirred at 100° C. overnight, cooled to room temperature, poured into brine (30 mL), and extracted with EtOAc (40 mL×3). The combined organic layers were washed with brine (100 mL), dried over Na$_2$SO$_4$, and concentrated in vacuo. The residual solid was purified by column chromatography on silica gel (hexane/acetone=7/3 to 1/1) to afford the title compound 16 as a foam.

EXAMPLE 15
Synthesis of Carboxylic Acid (17)

A solution of concentrated sulfuric acid (3 mL) in water (7 mL) was added to the nitrile 16 (0.95 g, 2.90 mmol) at room temperature. After being stirred at 85° C. for 2 days, the mixture was cooled to room temperature, pH adjusted to pH 3 with K$_2$CO$_3$ (solid), and extracted with EtOAc (60 mL×2). The organic layer was dried over Na$_2$SO$_4$, and concentrated in vacuo. The residual solid was triturated with EtOAc (50 mL) and hexane (50 mL) to afford the title compound 17 as a solid.

EXAMPLE 16
Synthesis of trans-4-(3-iodopyridin-4-yl)-4-hydroxy-N-[5-(2-fluorophenyl)-2-pyrimidinyl]-cyclohexanecarboxamide 2-Chloro-1,3-dimethyl-2-imidazolinium chloride (0.37 g, 2.19 mmol) was added to a mixture of the carboxylic acid 17 (0.69 g, 1.99 mmol) and 2-amino-5-(2-fluorophenyl) pyrimidine 11 (0.34 g, 1.80 mmol) in chloroform (3.0 mL) and pyridine (3.0 mL), and the mixture was stirred overnight. The reaction mixture was diluted with ethyl acetate (60 mL), and washed with 10% citric acid (60 mL), saturated NaHCO$_3$ (60 mL) and brine (60 mL). The aqueous layer was extracted with EtOAc (60 mL×2). The combine organic layers were washed with water (60 mL), saturated NaHCO$_3$ (60 mL), brine (60 mL), dried over Na$_2$SO$_4$ and concentrated in vacuo. The residue was purified by chromatography on silica gel (EtOAc to MeOH/CHCl$_3$=1/19), and triturated with EtOAc to afford the title compound as a solid.

EXAMPLE 17

[$^{11}$C]trans-N-[5-(2-fluorophenyl)-2-pyrimidinyl]-3-oxospiro[5-azaisobenzofurane-1(3H),1'-cyclohexane]-4'-carboxamide

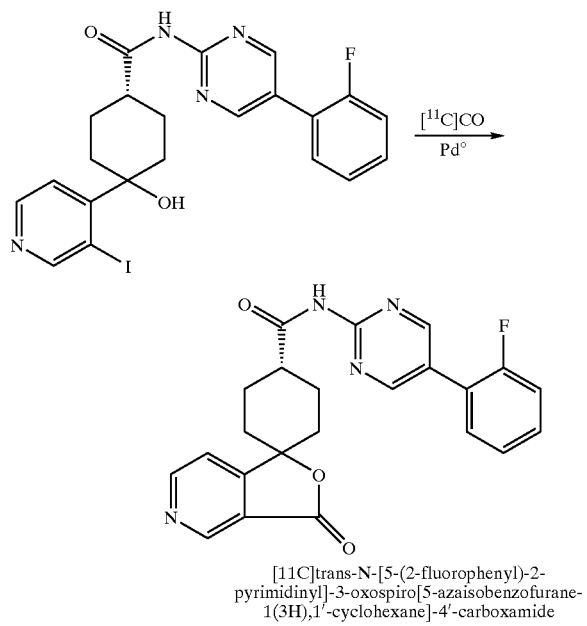

[11C]trans-N-[5-(2-fluorophenyl)-2-pyrimidinyl]-3-oxospiro[5-azaisobenzofurane-1(3H),1'-cyclohexane]-4'-carboxamide

[$^{11}$C]trans-N-[5-(2-fluorophenyl)-2-pyrimidinyl]-3-oxospiro[5-azaisobenzofurane-1(3H),1'-cyclohexane]-4'-carboxamide was prepared as for Example 10 from the iodide from Example 16.

References and Notes (1) References for lithiopyridines

G. W. Grible, M. G. Saulnier, *Tetrahedron Lett.* 1980, 21, 4137–4140; M. Mallet, G. Quéguiner, *Tetrahedron* 1982, 38, 3035–3042; E. J. Corey, S. G. Pyne, A. I. Schafer, *Tetrahedron Lett.* 1983,24, 3291–3294; K. Jones, A. Fiumana *Tetrahedron Lett.* 1996, 37, 8049–8052; G. W. Grible, M. G. Saulnier, *Heterocycles* 1993, 35, 151–169; F. Effenberger, W. Daub, *Chem. Ber.,* 1991, 124, 2119–2125; Y. Miki, Y. Tada, K. Matsushita, *Heterocycles* 1998, 48, 5483–5486.

(2) When 4-cyclohexanonecarboxylic acid ethyl ester was reacted with the lithiopyridine derived from 3-bromopyridine and LDA, significant enolate formation took place, resulting in recovery of alot of 4-cyclohexanonecarboxylic acid ethyl ester.

(3) The stereochemistry of ethyl ester of compound 8 was confirmed by $^1$H NMR experiments.

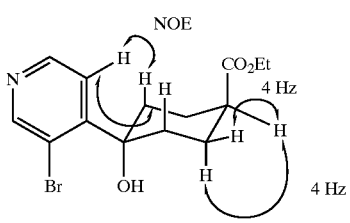

(4) When the cis isomer is included in the trans isomer of ethyl ester of compound 8, the ratio of the diastereomers can be determined by $^1$H NMR, which shows two doublet peaks at 7.55 and 7.62 ppm corresponding to C-5 proton on pyridine ring.

(5) Retention times for the cis isomer of 8 and compound 8 are 6.4 min and 4.3 min, respectively. HPLC conditions are as follows:

Column: Waters Symmetory C-18 (5 μm), 4.6 mm i.d.×250 mm
Mobile phase: A/B=65/35 to 30/70 from 0 to 10 min. linear gradient
A=50 mM aqueous $HCOONH_4$ (pH 3.5 adjusted with HCOOH)
B=MeCN/water=50/7
Flow rate: 1.0 mL/min.
Column temp: 40° C.
Detection: UV 254 nm While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compound of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed:

1. A compound which is trans-N-[5-(2-fluorophenyl)-2-pyrimidinyl]-3-[$^{11}$C]-oxospiro[5-azaisobenzofurane-1(3H), 1'-cyclohexane]-4'-carboxamide or a pharmaceutically acceptable salt thereof.

2. A radiopharmaceutical composition which comprises the compound of claim 1 and at least one pharmaceutically acceptable carrier or excipient.

3. A method for the diagnostic imaging of neuropeptide Y Y5 receptors in a mammal which comprises administering to a mammal in need of such diagnostic imaging an effective amount of the compound of claim 1.

4. The method of claim 3 wherein the mammal is a human.

5. A method for the diagnostic imaging of the brain in a mammal which comprises administering to a mammal in need of such diagnostic imaging an effective amount of the compound of claim 1.

6. The method of claim 5 wherein the mammal is a human.

7. A method for the diagnostic imaging of tissues bearing neuropeptide Y Y5 receptors in a mammal which comprises administering to a mammal in need of such diagnostic imaging an effective amount of the compound of claim 1.

8. The method of claim 7 wherein the mammal is a human.

9. A method for the quantification of neuropeptide Y Y5 receptors in mammalian tissue which comprises contacting such mammal tissue in which such quantification is desired with an effective amount of the compound of claim 1.

10. The method of claim 9 wherein the mammalian tissue is human tissue.

* * * * *